United States Patent [19]
Yan et al.

[11] Patent Number: 6,140,500
[45] Date of Patent: Oct. 31, 2000

[54] RED-EMITTING [8,9]BENZOPHENOXAZINE NUCLEIC ACID DYES AND METHODS FOR THEIR USE

[75] Inventors: Xiongwei Yan, Belmont; Sheri Miragila, Palo Alto; Pau Miau Yuan, San Jose, all of Calif.

[73] Assignee: PE Corporation, Foster City, Calif.

[21] Appl. No.: 09/389,918

[22] Filed: Sep. 3, 1999

[51] Int. Cl.⁷ ..................... C07D 265/34; C07D 265/28
[52] U.S. Cl. ................................. 544/99; 544/98
[58] Field of Search ................... 544/1, 99, 102, 544/103

[56] References Cited

U.S. PATENT DOCUMENTS

| | | | |
|---|---|---|---|
| 4,237,281 | 12/1980 | Long | 544/99 |
| 4,386,149 | 5/1983 | Mason et al. | 430/213 |
| 4,622,395 | 11/1986 | Bellus et al. | 544/37 |
| 4,962,197 | 10/1990 | Foley et al. | 544/31 |
| 5,436,134 | 7/1995 | Haughland et al. | 435/29 |
| 5,565,554 | 10/1996 | Glazer et al. | 536/26.6 |
| 5,783,687 | 7/1998 | Glazer et al. | 536/26.6 |
| 5,876,946 | 3/1999 | Burbaum et al. | 435/7.1 |

FOREIGN PATENT DOCUMENTS

| | | |
|---|---|---|
| 9729254 | 8/1997 | WIPO . |
| WO97/29154 | 8/1997 | WIPO . |

OTHER PUBLICATIONS

Becker et al., "The Photosensitizers Benzophenoxazine and Thiazines: Comprehensive Investigation of Photophysical and Photochemical Properties," *Photochemistry and Photobiology* 51(5):533–538 (1990).

Cincotta et al., "Novel Red Absorbing Benzo[a]phenoxazinium and Benzo[a]phenothiazinium Photosensitizers: in vitro Evaluation," *Photochemistry and Photobiology* 46(5):751–758 (1987).

Polášek, "Amperometric Glucose Sensor Based on Glucose Dehydrogenase Immobilized on a Graphite Electrode Modified With an N,N'–bis(benzophenoxazinyl) deriative of benzene–1,4–dicarboxamide," *Analytica Chimica Acta.* 246:283–292 (1991).

Webster's Newworld Dictionary of the American Language, 2nd College Edn., Jan. 1986.

*Primary Examiner*—Mukund J. Shah
*Assistant Examiner*—Sudhaker B. Patel
*Attorney, Agent, or Firm*—Alex Andrus; Ann Pease

[57] ABSTRACT

A new class of red-emitting, fluorescent [8,9] benzophenoxazine dyes are provided that are useful for staining nucleic acids in a variety of contexts, including in solutions, in electrophoretic gels or other matrices, in blotting experiments and in assays employing intact, live cells. The new dyes are brighter and permeate cells faster than currently available red-emitting live-cell nucleic acid stains.

34 Claims, 2 Drawing Sheets

RED-EMITTING [8,9] BENZOPHENOXAZINE NUCLEIC ACID DYES AND METHODS FOR THEIR USE

1. FIELD OF THE INVENTION

The present invention relates to fluorescent red-emitting [8,9]benzophenoxazine dyes useful for staining, labeling and/or detecting nucleic acids.

2. BACKGROUND OF THE INVENTION

Many areas of basic research benefit from the ability to rapidly and sensitively detect nucleic acids. For example, in many fields of life sciences research, including biological, biomedical, genetic, fermentation, aquaculture, agriculture, forensic and environmental research, there is a need to identify nucleic acids both within and without cells as a routine component of standard experimental methods. A common example is the widespread use of gel electrophoresis for characterizing nucleic acids, one limitation of which is the sensitivity of the staining method used to detect the nucleic acid bands.

In the life and medical sciences, researchers and technicians often need to identify intracellular nucleic acids and/or sort cells based on the quantity of nucleic acids present in the cells. The quantity of nucleic acids present can be indicative of the type of cells, or even the presence of disease states in cells (e.g., nucleated human erythrocytes). Such applications require a fast, sensitive and selective methodology that can detect nucleic acids, even when bounded (or surrounded) by cellular membranes.

Dyes that are generally applicable for staining nucleic acids across a broad range of applications preferably have the following properties:

i) the nucleic acid-dye complex should produce a very high signal with low background so that small quantities of nucleic acids can be sensitively detected in both cell-free and cell-based assays; and ii) the nucleic acid-dye complex should be photostable so that the fluorescent signal may be observed, monitored and recorded without significant photo bleaching.

For applications involving staining nucleic acids in cells, especially live cells, the dyes should preferably have the following additional properties:

iii) the dye should be permeable to cell membranes so that it can bind nucleic acids sequestered in cells;

iv) the membrane permeation kinetics should be relatively fast so that detectable signals can be obtained upon relatively brief exposures to the dye; and v) the dye should be non-toxic to living cells so that staining will not disrupt the normal metabolic processes of the cells or cause premature cell death.

A variety of dyes useful for staining nucleic acids in cell-free and/or intracellular assays have been described. For example, a variety of asymmetrical cyanine dyes (Brooker et al., 1942, J. Am. Chem. Soc. 64:199) and thioflavin dyes (U.S. Pat. Nos. 4,554,546 and 5,057,413) useful for staining nucleic acids have been described. The non-chimeric asymmetrical cyanine dye sold under the trade name Thiazole Orange provides particular advantages in the quantitative analysis of immature blood cells or reticulocytes (U.S. Pat. No. 4,883,867) and in preferentially staining nucleic acids of blood-borne parasites (U.S. Pat. No. 4,937,198). Although Thiazole Orange and other thioflavin cyanine dyes are permeable to membranes of many mammalian cells, they are non-permeable to many eukaryotic cells.

Other related cyanine dyes have been described which are non-permeable to living cells unless their membranes have been disrupted (see, U.S. Pat. Nos. 5,321,130 and 5,410,030). A variety of dimeric dyes having cationic moieties useful for staining nucleic acids in electrophoretic gels are described in U.S. Pat. Nos. 5,312,921; 5,401,847; 5,565,554; and 5,783,687.

Substituted asymmetric cyanine dyes capable of permeating membranes of a broad spectrum of both living and dead cells have also been described (see, U.S. Pat. No. 5,436,134).

While many of these dyes have found use as nucleic acid stains, they suffer several drawbacks which limit their general applicability, particularly in live-cell assays. For example, most of the available dyes fluoresce in the green region of the visible spectrum. Not only are green lasers more expensive than red lasers, green fluorescence results in higher background signals in live cell assays due to, among other factors, autofluorescence of cellular components and assay equipment. These higher background signals decrease the sensitivity of the assay. Moreover, many cellular components absorb green light, further reducing the sensitivity of the assay.

Since red lasers are less expensive than green lasers and cellular components are generally transparent to red light, nucleic acid stains that have excitation and emission maxima in the red region of the visible spectrum are preferred for live-cell assays. However, the availability of membrane permeable red-emitting nucleic acid stains having suitable properties for live-cell assays is limited. Unfortunately, the most common water-soluble red-emitting dyes, the cyanine dyes such as dye Cy5, are not photostable. Thus, sensitive nucleic acid stains that are photostable, have excitation and emission maxima in the red region of the visible spectrum and that are permeable to cell membranes are highly desirable.

3. SUMMARY OF THE INVENTION

Dyes having these and other advantageous properties are afforded by the present invention, which in one aspect provides a new class of red-emitting [8,9]benzophenoxazine dyes for labeling, staining and/or detecting nucleic acids. The new [8,9]benzophenoxazine dyes of the invention are characterized by an aliphatic cationic chain linked to a parent [8,9]benzophenoxazine ring. The parent [8,9] benzophenoxazine ring contains two nitrogenous substituents: an amino substituent at the C3 carbon and an imminium substituent at the C7 carbon. The C3 amino substituent may be a primary, secondary or tertiary amino group. When the amino group is a secondary or tertiary amino, the nitrogen substituents are one or more of the same or different ($C_5$–$C_{14}$) aryl or ($C_1$–$C_6$) alkyl groups, more preferably one or more of the same or different ($C_1$–$C_6$) alkanyl group. Alternatively, the nitrogen may be included in an aliphatic ring, in which instance the amino nitrogen is substituted with an aliphatic bridge, typically a ($C_2$–$C_8$) alkyldiyl or ($C_2$–$C_6$) alkyleno. The cationic chain, which is described in more detail below, is attached to the C7 imminium nitrogen via a methylene carbon.

The parent [8,9]benzophenoxazine ring can be independently substituted at the C1, C2, C4, C6, C11, C12, C13 and/or C14 positions with a wide variety of different substituents, which may be the same or different. Any such substituents should generally be uncharged so as not to deleteriously affect the ability of the dye to permeate through, or diffuse across, cell membranes. Typical substituents are selected from the group consisting of halogen, ($C_1$–$C_6$) alkyl, —OR, —SR, —NRR, —CN, —NO$_2$ and —C(O)R, where each R is independently hydrogen or ($C_1$–$C_6$) alkyl. Such substituents can be used to adjust or fine-tune the excitation and/or emission spectral properties of the dyes for particular applications and equipment. Moreover, the parent [8,9]benzophenoxazine ring may contain one or more ($C_5$–$C_{14}$) aryleno bridges fused to the C1 and C2 carbons; the C11 and C12 carbons; the C12 and C13 carbons; and/or the C13 and C14 carbons. Adding such aryleno bridge substituents to the parent [8,9] benzophenoxazine ring generally shifts the excitation and emissions maxima of the dye to the red. These aryleno bridges may also be further substituted with one or more of the same or different uncharged groups, as described above.

The aliphatic cationic chain typically comprises a total of about 4 to 20 non-hydrogen atoms and has from 1 to 4 heteroatoms which contribute positive charges under the conditions in which the dye is used. Not including the positive charge contributed by the C7 imminium nitrogen of the parent [8,9]benzophenoxazine ring, the cationic chain has at least 1 positive charge and usually not more than 4 positive charges, more typically not more than 3 positive charges under the conditions in which the dye is used. In embodiments in which the parent [8,9]benzophenoxazine ring comprises a total of 4 fused rings, the cationic chain preferably has 1 or 2 positive charges, not including the positive charge contributed by the C7 imminium nitrogen. In embodiments in which the parent [8,9]benzophenoxazine ring comprises a total of 5 fused rings, the cationic chain preferably has 1 or 3 positive charges, not including the positive charge contributed by the C7 imminium nitrogen. The positive charges are typically based upon amino or imino groups, although other elements which can support a positive charge, such as sulfur, phosphorous and iodine, may also be used to the extent that these cations are stable under the conditions of use.

As even primary amino or imino groups are basic enough to contribute at least a partial positive charge at the typical pHs of use (i.e., pHs in the range of pH 6 to pH 9), the amino or imino groups, which are either internal to the aliphatic chain or at a terminus, may be either substituted or unsubstituted. As the basicity of amino and imino groups generally increases with increased substitution, the internal amino groups are preferably at least mono-substituted and the terminal amino groups are preferably at least di-substituted. Terminal imino groups are preferably at least mono-substituted. Alternatively, the amino or imino groups may be fully substituted (i.e., quaternary amino or tertiary imino) such that they carry a permanent positive charge. When the cationic chain comprises only a single internal amino group, it is preferably a quaternary amino (di-substituted). When the cationic chain comprises more than one internal amino group, at least one of these groups should be a quaternary amino. Any terminal amino groups may be primary, secondary, tertiary or quaternary amino groups, but are preferably tertiary (di-substituted) or quaternary.

Virtually any substituent can be used to substitute the nitrogen atoms of the internal and terminal amino or imino groups. Usually, the nitrogen atoms are each independently substituted with one or more of the same or different ($C_1$–$C_6$) alkyl groups. Preferably, the nitrogen atoms are each independently substituted with one or more of the same or different straight-chain ($C_1$–$C_3$) alkanyl groups, most preferably one or more methanyl groups. Thus, the internal amino and imino groups are typically of the formula —NRR— and =NR—, respectively, and the terminal amino and imino groups are typically of the formula —NRRR and =NRR, respectively, where each R is independently hydrogen or ($C_1$–$C_6$) alkyl.

The amino or imino groups of the cationic chain are usually separated from one another by as few as 2 to as many as 6 carbon atoms. Typically, the amino or imino groups of the cationic chain are separated by 2 or 3 carbon atoms. Likewise, the C7 imminium nitrogen is separated from an amino or imino group by as few as 2 to as many as 6 carbon atoms, preferably by 3 carbon atoms. The cationic chain may contain any number of carbon-carbon double bonds, carbon-nitrogen double bonds or carbon-carbon triple bonds, but is preferably saturated. Moreover, the cationic chain is typically linear, with the only branch points occurring at the amino or imino groups. However, the backbone carbon atoms may contain one or more of the same or different ($C_1$–$C_6$) alkyl substituents.

The new [8,9]benzophenoxazine dyes of the invention can be used as intercalating or non-intercalating dyes to stain or label nucleic acids for subsequent detection in a broad range of contexts, including, e.g., in solutions, in electrophoretic gels, on blots and in other assays. While not intending to be bound by any particular theory of operation, when the dyes are used as intercalating dyes or stains, such as, for example to stain double-stranded DNA or RNA, their ability to bind nucleic acids is believed to be mediated largely by the parent [8,9]benzophenoxazine ring intercalating between base pairs. When the dyes are used as non-intercalating dyes or stains, such as, for example, to stain single-stranded DNA or RNA, their ability to bind nucleic acids is believed to be mediated largely by ionic attraction between the anionic phosphodiester backbone of the nucleic acid and the cationic chain of the dye. However, those of skill in the art will recognize that both ionic and hydrophobic interactions, as well as other types of interactions, are likely involved in binding both single-stranded and double-stranded nucleic acids. The most preferred dyes of the invention are those that are membrane permeable.

The new [8,9]benzophenoxazine dyes of the invention possess several properties which make them ideally suited for staining nucleic acids across a broad range of applications. For example, the new [8,9]benzophenoxazine dyes of the invention: (i) have high molar absorptivities, with extinction coefficients of $\geq 50,000$ cm$^{-1}$M$^{-1}$ in the red region ($\geq 630$ nm) of the visible spectrum; (ii) have long emissions wavelengths, typically $\geq 650$ nm, depending upon the substitution pattern of the parent [8,9]benzophenoxazine ring; (iii) have excellent photostability properties; (iv) produce a dramatic increase in quantum yield upon binding nucleic acids, typically being significantly brighter than available and/or reported nucleic acid stains; and (v) have a high binding affinity for both single-stranded and double-stranded nucleic acids.

In addition to these desirable properties, most of the [8,9]benzophenoxazine dyes of the invention are capable of passively permeating through, or diffusing across, membranes of intact live cells, making them ideally suited for live-cell staining of both DNAs and RNAs. To date, the membrane-permeable dyes of the invention have exhibited good permeability in all cell lines tested. Quite significantly, the new [8,9]benzophenoxazine dyes traverse cell membranes at rates significantly faster than currently available live-cell nucleic acid stains. Direct comparison of the rate of uptake in HCT-116 cells between two [8,9] benzophenoxazine dyes of the invention with the known cyanine dye SYTO 61® (Molecular Probes, Eugene, Oreg.) shows significantly faster rate-of-uptake by the new dyes of the invention (FIG. 2).

Moreover, eukaryotic cells stained with the dyes of the invention may exhibit greater than 1000-fold more fluorescence than cells stained with conventional cyanine dyes such as SYTO 61®. Owing to their brighter signals and enhanced permeation kinetics, the new [8,9]benzophenoxazine dyes of the invention provide faster results with far less dye in live-cell nucleic acid assays than currently available dyes. Moreover, by simple synthetic modification of the cationic chain and/or substituents attached to the parent [8,9] benzophenoxazine ring, dyes having favorable permeability characteristics and absorption and emission spectral properties in the red region of the visible spectrum can be readily obtained. Thus, the [8,9]benzophenoxazine dyes of the invention represent a new class of photostable, visibly-excitable, live-cell nucleic acid stains that overcome many of the shortcomings of currently available live-cell nucleic acid stains.

4. BRIEF DESCRIPTION OF THE DRAWINGS

Figure 1:
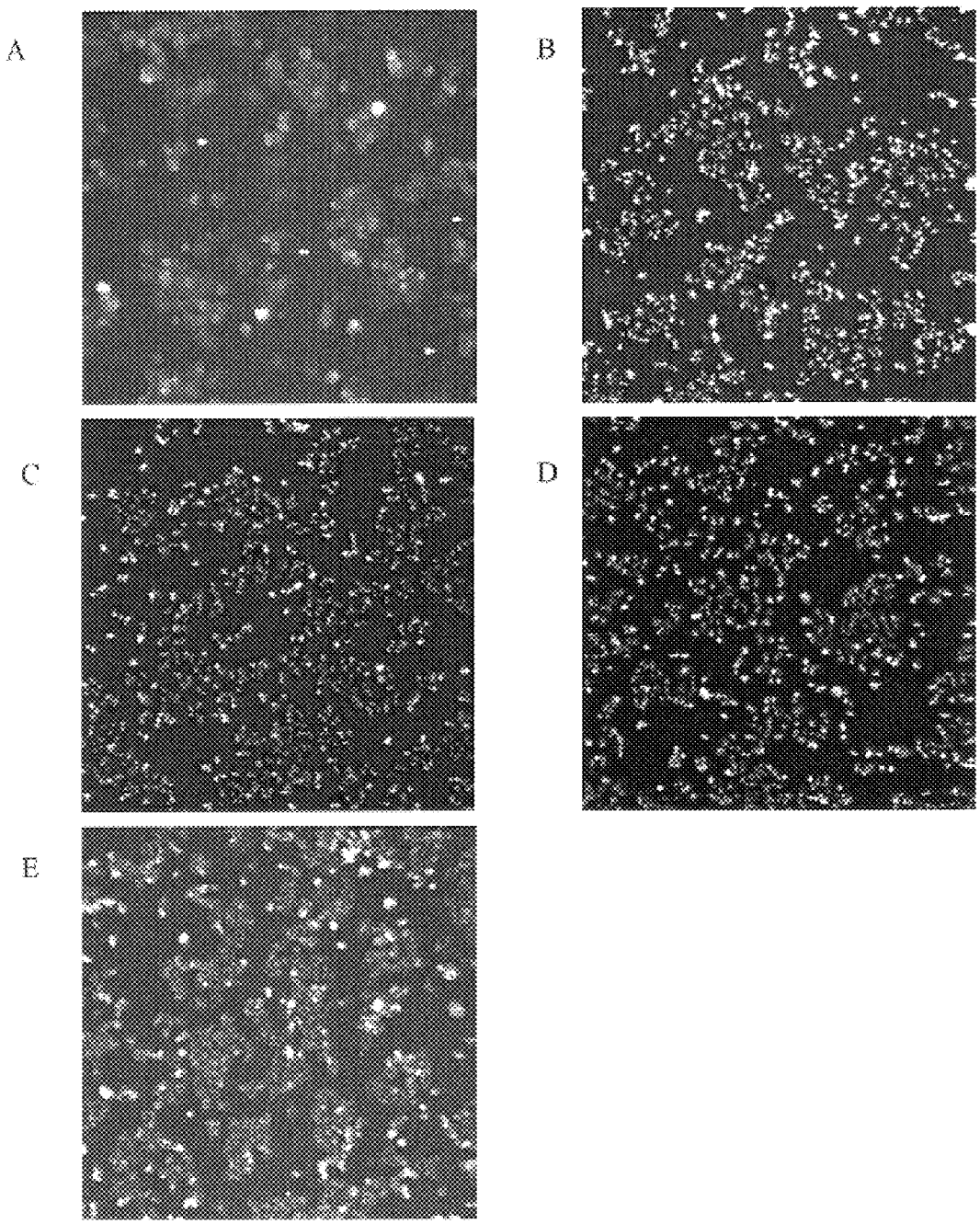
FIG. 1A is a photograph of HCT-116 cells stained with 0.57 μg/mL Cy5-labeled antibody anti HLA-A,B,C.
FIG. 1B is a photograph of HCT-116 cells stained with 20 nM Bona 12.
FIG. 1C is a photograph of HCT-116 cells stained with 20 nM Bona 24.
FIG. 1D is a photograph of HCT-116 cells stained with 20 nM Bona 25.
FIG. 1E is a photograph of HCT-116 cells stained with 4 nM SYTO 61® (Molecular Probes, Eugene, Oreg.)

5. DETAILED DESCRIPTION OF THE PREFERRED EMBODIMENTS 5.1 Numbering System

For purposes of the present application, the parent [8,9] benzophenoxazine ring is numbered as follows:

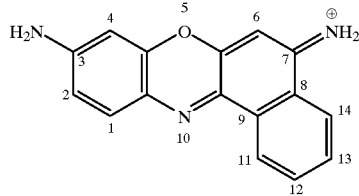

5.2 Definitions

As used herein, the following terms are intended to have the following meanings:

"Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl (methanyl); ethyls such as ethanyl, ethenyl, ethynyl; propyls such as propan-1-yl, propan-2-yl (isopropyl), cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl (sec-butyl), 2-methyl-propan-1-yl (isobutyl), 2-methyl-propan-2-yl (t-butyl), cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, but-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below.

"Alkanyl:" refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl, 2-methyl-propan-1-yl (isobutyl), 2-methyl-propan-2-yl (1-butyl), cyclobutan-1-yl, etc.; and the like.

"Alkenyl:" refers to an unsaturated branched, straight-chain or cyclic alkyl radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl:" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl etc.; and the like.

"Aromatic Ring System:" refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Aryl:" refers to a monovalent aromatic hydrocarbon radical derived by the removal of one hydrogen atom from a single carbon atom of an aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleadene, pyrene, pyranthrene, rubicene, triphenylene, trinaphthalene, and the like. In preferred embodiments, the aryl group is ($C_5$–$C_{20}$) aryl, with ($C_5$–$C_{10}$) being even more preferred. Particularly preferred aryls are phenyl ($C_6$ aryl) and naphthyl ($C_{10}$ aryl).

"Aryleno:" refers to a divalent bridge radical having two adjacent monovalent radical centers derived by the removal of one hydrogen atom from each of two adjacent carbon atoms of a parent aromatic ring system. Attaching an aryleno bridge radical, e.g. benzeno, to a parent aromatic ring system, e.g. benzene, results in a fused aromatic ring system, e.g. naphthalene. The bridge is assumed to have the maximum number of non-cumulative double bonds consistent with its attachment to the resultant fused ring system. When an aryleno substituent is formed by taking together two adjacent substituents on a structure that includes alternative substituents, to avoid double-counting carbon atoms, the carbon atoms of the aryleno bridge replace the bridging carbon atoms of the structure. As an example, consider the following structure:

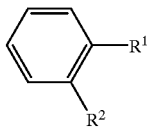

wherein:

$R^1$, when taken alone is hydrogen, or when taken together with $R^2$ is $(C_5-C_{14})$ aryleno;

and $R^2$, when taken alone is hydrogen, or when taken together with $R^1$ is $(C_5-C_{14})$ aryleno.

When $R^1$ and $R^2$ are each hydrogen, the resultant compound is benzene. When $R^1$ taken together with $R^2$ is $C_6$ aryleno (benzeno), the resultant compound is naphthalene. When $R^1$ taken together with $R^2$ is $C_{10}$ aryleno (naphthaleno), the resultant compound is anthracene or phenanthrene. Typical aryleno groups include, but are not limited to, aceanthryleno, acenaphthyleno, acephenanthryleno, anthraceno, azuleno, benzeno (benzo), chryseno, coroneno, fluorantheno, fluoreno, hexaceno, hexapheno, hexaleno, as-indaceno, s-indaceno, indeno, naphthaleno (naphtho), octaceno, octapheno, octaleno, ovaleno, penta-2,4-dieno, pentaceno, pentaleno, pentapheno, peryleno, phenaleno, phenanthreno, piceno, pleladeno, pyreno, pyranthreno, rubiceno, triphenyleno, trinaphthaleno, and the like. Where a specific connectivity is intended, the involved bridging carbon atoms (of the aryleno bridge) are denoted in brackets, e.g., [1,2]benzeno ([1,2] benzo), [1,2]naphthaleno, [2,3]naphthaleno, etc.

5.3 Due Compounds Per Se

The present invention provides a new class of [8,9] benzophenoxazine dyes useful for staining or labeling nucleic acids for subsequent detection. As described in the Summary section, the new dyes generally comprise a substituted or unsubstituted parent [8,9]benzophenoxazine ring and an aliphatic cationic chain. In a preferred embodiment of the invention, the [8,9]benzophenoxazine dyes are compounds according to structural formula (I):

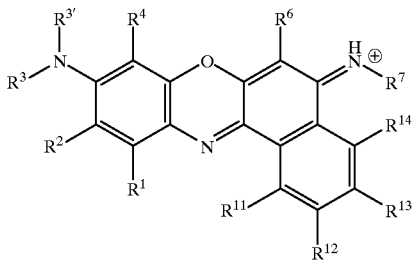

including any associated counterions, wherein:

$R^1$, when taken alone, is selected from the group consisting of hydrogen, halogen, $(C_1-C_6)$ alkyl, —OR', —SR', —NR'R', —CN, —NO$_2$ and —C(O)R', or when taken together with $R^2$ is $(C_5-C_{14})$ aryleno or $(C_5-C_{14})$ aryleno substituted with one or more of the same or different W groups;

$R^2$, when taken alone, is selected from the group consisting of hydrogen, $(C_1-C_6)$ alkyl, —OR', —SR', —NR'R', —CN, —NO$_2$ and —C(O)R', or when taken together with $R^1$ is $(C_5-C_{14})$ aryleno or $(C_5-C_{14})$ aryleno substituted with one or more of the same or different W groups;

$R^3$, when taken alone, is selected from the group consisting of hydrogen, $(C_1-C_6)$ alkyl and $(C_5-C_{14})$ aryl, or when taken together with $R^{3'}$ is $(C_2-C_8)$ alkyldiyl or $(C_2-C_6)$ alkyleno;

$R^{3'}$, when taken alone, is selected from the group consisting of hydrogen, $(C_1-C_6)$ alkyl and $(C_5-C_{14})$ aryl or when taken together with $R^3$ is $(C_2-C_8)$ alkyldiyl or $(C_2-C_6)$ alkyleno;

$R^4$ is selected from the group consisting of hydrogen, $(C_1-C_6)$ alkyl, —OR', —SR', —NR'R', —CN, —NO$_2$ and —C(O)R';

$R^6$ is selected from the group consisting of hydrogen, $(C_1-C_6)$ alkyl, —OR', —SR', —NR'R', —CN, —NO$_2$ and —C(O)R';

$R^7$ is an aliphatic cationic chain, as previously described;

$R^{11}$, when taken alone, is selected from the group consisting of hydrogen, $(C_1-C_6)$ alkyl, —OR', —SR', —NR'R', —CN, —NO$_2$ and —C(O)R', or when taken together with $R^{12}$ is $(C_5-C_{14})$ aryleno or $(C_5-C_{14})$ aryleno substituted with one or more of the same or different W groups;

$R^{12}$, when taken alone, is selected from the group consisting of hydrogen, $(C_1-C_6)$ alkyl, —OR', —SR', —NR'R', —CN, —NO$_2$ and —C(O)R', or when taken together with $R^{11}$ or $R^{13}$ is $(C_5-C_{14})$ aryleno or $(C_5-C_{14})$ aryleno substituted with one or more of the same or different W groups;

$R^{13}$, when taken alone, is selected from the group consisting of hydrogen, $(C_1-C_6)$ alkyl, —OR', —SR', —NR'R', —CN, —NO$_2$ and —C(O)R', or when taken together with $R^{12}$ or $R^{14}$ is $(C_5-C_{14})$ aryleno or $(C_5-C_{14})$ aryleno substituted with one or more of the same or different W groups;

$R^{14}$, when taken alone, is selected from the group consisting of hydrogen, $(C_1-C_6)$ alkyl, —OR', —SR', —NR'R', —CN, —NO$_2$ and —C(O)R', or when taken together with $R^{13}$ is $(C_5-C_{14})$ aryleno or $(C_5-C_{14})$ aryleno substituted with one or more of the same or different W groups;

each W is independently selected from the group consisting of ($C_1$–$C_6$) alkyl, —OR', —SR', —NR'R', —CN, —$NO_2$ and —C(O)R'; and each R' is independently hydrogen or ($C_1$–$C_6$) alkyl.

One group of preferred compounds according to structural formula (I) are those compounds in which $R^7$ is —($CH_2$)$_n$—[NRR—($CH_2$)$_n$]$_m$—NRRR, where each n is independently an integer from 2 to 6, m is an integer from 0 to 6 and each R is independently selected from the group consisting of hydrogen and ($C_1$–$C_6$) alkyl.

Another group of preferred compounds according to structural formula (1) are those compounds which are capable of passively permeating through, or diffusing across, a membrane of a live prokaryotic or eukaryotic cell. When the cell is a eukaryote, such as a mammalian cell, the preferred dyes are even more preferably capable of passively permeating through, or diffusing across, the nuclear membrane and staining the nuclear nucleic acids of the cell.

The membrane-permeability of a dye of the invention can be readily tested by contacting one or more cells with a staining solution, e.g., phosphate-buffered saline, comprising the dye (staining solutions are discussed in more detail, infra) and assaying for a detectable signal. Generally, when a dye is membrane impermeable, the cells will appear as dark spots when detected using illuminators and detectors matched to the excitation and emission wavelengths of the dye being tested. Dyes which produce a detectable signal ($\geq$2–3 times background) in 5–10 min. when used in a staining solution (pH in the range of pH 6 to pH 8–9) at a concentration in the range of 10 pM to 100 nM (or even less) are considered membrane permeable. Dyes which produce very bright signals (i.e., $\geq$100 times background) at extremely low concentrations (i.e., $\leq$10 nM, or even less) in about 1–5 min. are particularly preferred, as these dyes provide increased sensitivity.

Still another group of preferred compounds according to structural formula (I) are those compounds which have one or more features selected from the following group of features:

$R^1$, $R^2$, $R^4$ and $R^6$ are each hydrogen;

$R^3$ and $R^{3'}$ are each independently ($C_5$–$C_{10}$) aryl or ($C_1$–$C_3$) alkanyl;

the aryleno group formed by taking $R_1$ together with $R^2$ is benzo, [1,2]naphthaleno or [2,3]naphthaleno;

the aryleno group formed by taking $R_{11}$ together with $R^{12}$ is benzo;

the aryleno group formed by taking $R^{12}$ together with $R^{13}$ is benzo;

the aryleno group formed by taking $R^{13}$ together with $R^{14}$ is benzo;

$R^{11}$, $R^{12}$, $R^{13}$ and $R^{14}$ are each hydrogen; and/or $R^7$ is selected from the group consisting of —($CH_2$)$_n$—NRRR, —($CH_2$)$_n$—NRR—($CH_2$)$_n$—NRRR and —($CH_2$)$_n$—NRR—($CH_2$)$_n$—NRR—($CH_2$)$_n$—NRRR, where each n is independently an integer from 2 to 3 and each R is independently selected from the group consisting of hydrogen and ($C_1$–$C_3$) alkanyl.

Another group of preferred compounds according to structural formula (I) are those compounds in which:

$R^1$, when taken alone, is hydrogen, or when taken together with $R^2$ is benzo, naphthaleno, [1,2]naphthaleno or [2,3]naphthaleno;

$R^2$, when taken alone, is hydrogen, or when taken together with $R^1$ is benzo, naphthaleno, [1,2]naphthaleno or [2,3]naphthaleno;

$R^3$ is ($C_1$–$C_3$) alkyl or ($C_1$–$C_3$) alkanyl;

$R^{3'}$ is ($C_1$–$C_3$) alkyl or ($C_1$–$C_3$) alkanyl;

$R^4$ is hydrogen;

$R^6$ is hydrogen;

$R^7$ is an aliphatic cationic chain, as previously described, preferably —($CH_2$)$_n$—NRRR, —($CH_2$)$_n$—NRR—($CH_2$)$_n$—NRRR or —($CH_2$)$_n$—NRR—($CH_2$)$_n$—NRR—($CH_2$)$_n$—NRRR, where each n is independently an integer from 2 to 3 and each R is independently selected from the group consisting of hydrogen and ($C_1$–$C_3$) alkanyl;

$R^{11}$, when taken alone, is hydrogen, or when taken together with $R^{12}$ is benzo;

$R^{12}$, when taken alone, is hydrogen, or when taken together with $R^{11}$ or $R^{13}$ is benzo;

$R^{13}$, when taken alone, is hydrogen, or when taken together with $R^{12}$ or $R^{14}$ is benzo; and $R^{14}$, when taken alone, is hydrogen, or when taken together with $R^{13}$ is benzo.

Yet another group of preferred compounds according to structural formula (I) are compounds according to structural formulae (II) and (III):

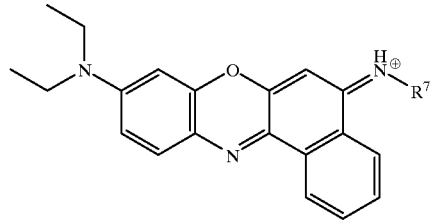

(II)

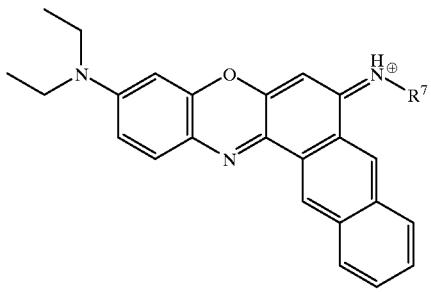

(III)

including any associated counterions, wherein $R^7$ is as previously described for structural formula (I). Compounds according to structural formula (II) typically have excitation (absorbance) maxima in the range of 630–650 nm and emissions maxima in the range of 660–680 nm, whereas compounds according to structural formula (III) typically have excitation (absorbance) maxima in the range of 650–660 nm and emissions maxima in the range of 680–720 nm, depending on the buffer, pH, temp. and other sample conditions (see, e.g., TABLE 1, Section 6.2, page 33, infra).

Preferred compounds according to structural formulae (II) and (III) are those compounds in which $R^7$ is selected from the group consisting of —($CH_2$)$_n$—NRRR, —($CH_2$)$_n$—NRR—($CH_2$)$_n$—NRRR and —($CH_2$)$_n$—NRR—($CH_2$)$_n$—NRR—($CH_2$)$_n$—NRRR, where each n is independently an integer from 2 to 3 and each R is independently selected from the group consisting of hydrogen, ($C_1$–$C_3$) alkanyl and methanyl.

Particularly preferred compounds according to structural formula (II) that exhibit good membrane permeability are illustrated below:
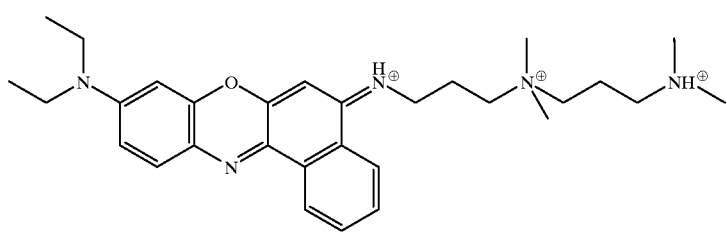
Bona 11
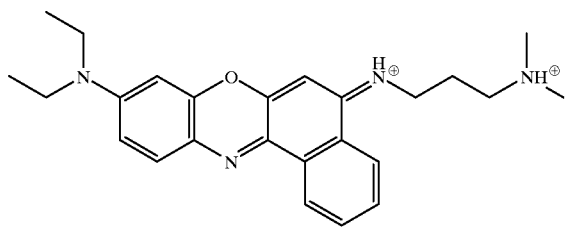
Bona 12
Particularly preferred compounds according to structural formula (III) that exhibit good membrane permeability are illustrated below:
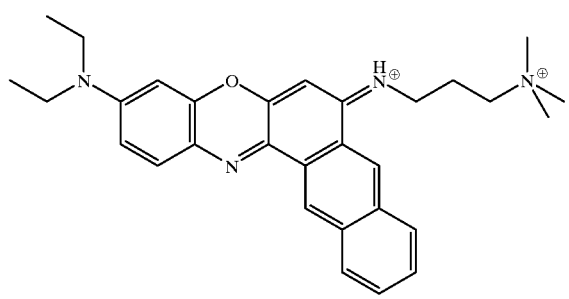
Bona 22
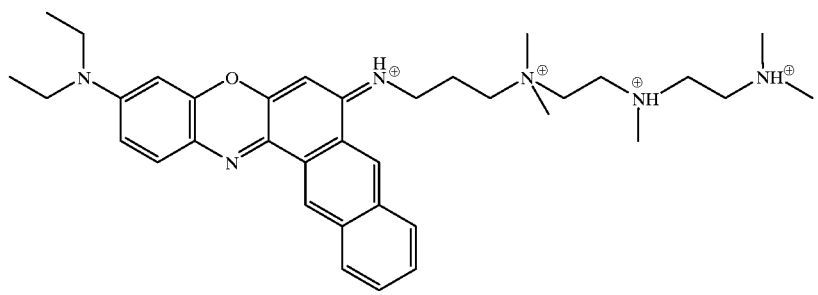
Bona 24
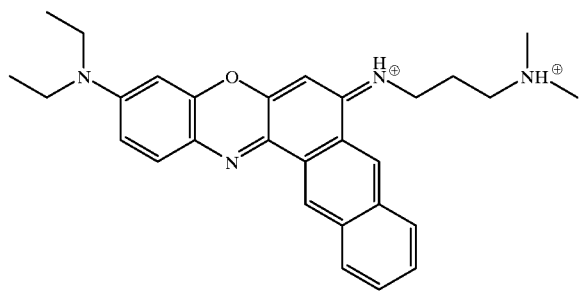
Bona 25

Those of skill in the art will appreciate that many of the compounds encompassed by formulae (I), (II) and (III), as well as the compound species specifically described above, may exhibit the phenomena of tautomerism, conformational isomerism, geometric isomerism and/or stereo isomerism. As the formulae drawings within this specification and claims can represent only one of the possible tautomeric, conformational isomeric, enantiomeric or geometric isomeric forms, it should be understood that the invention encompasses any tautomeric, conformational isomeric, enantiomeric and/or geometric isomeric forms of the compounds having one or more of the utilities described herein.

As a specific example, reference is made throughout the specification to C3 amino and C7 imminium substituents. As this nomenclature corresponds to the illustrated structural formulae, which represent only one of several possible tautomeric forms (or resonance structures) of the compounds, it will be understood that these references are for convenience only, and that any such references are not intended to limit the scope of the compounds described herein.

In addition, those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

As the compounds of the invention may bear multiple positive charges, depending upon their physical state, they may have counterions associated therewith. The identity(ies) of any associated counterions is typically dictated by the synthesis and/or isolation methods by which the compounds are obtained. Typical counterions include, but are not limited to, halides, acetate, trifluoroacetate, etc., and mixtures thereof. It will be understood that the identity(ies) of any associated counterions is not a critical feature of the invention, and that the invention encompasses the dyes in association with any type of counter ion. Moreover, as the compounds can exists in a variety of different forms, the invention is intended to encompass not only forms of the dyes that are in association with counterions (e.g., dry salts), but also forms that are not in association with counterions (e.g., aqueous or organic solutions).

5.4 Methods of Synthesizing the Compounds

The [8,9]benzophenoxazine dyes of the invention can be conveniently synthesized from iodo precursors, as illustrated in Schemes (I) and (II), below. Scheme (I) illustrates the synthesis of the iodo precursors. Scheme (II) illustrates the use of the iodo precursors to obtain the [8,9] benzophenoxazine dyes of the invention. In Schemes (I) and (II), the various $R^n$ are as previously defined for structural formula (I).

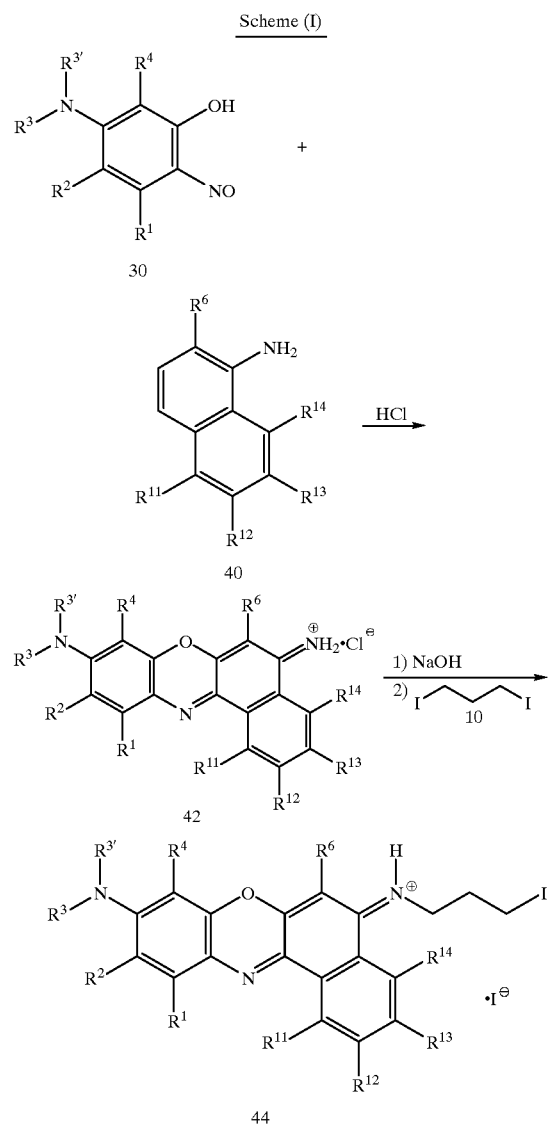

Referring to Scheme (I), 3-hydroxy-2-nitroso aniline derivative 30 (10 mM), 1-aminonaphthalene derivative 40 (10 mM) and HCl (0.24 M) are refluxed in methanol for approx. 2–50 hr to yield [8,9]benzophenoxazine derivative 42, which is isolated by flash silica gel column chromatography using methanol:methylene chloride as the eluent.

[8,9]Benzophenoxazine derivative 42 (approx. 60 mM in water at approx. 60° C.) is then treated with an equal volume of aqueous NaOH (0.5 M). The reaction is extracted 3× with methylene chloride (100 ml), the combined extracts dried with brine followed by anhydrous sodium sulfate, and the residual solvent removed by evaporation to yield the basic form of compound 42. This basic compound 42 (0.2 mmol) is dissolved in anhydrous toluene (5 ml), 1,3-diiodopropane 10 (2.0 mmol) added and the mixture refluxed under argon for approx. 16 hr. Iodo precursor 44 isolated by flash silica gel column chromatography using methanol:methylene chloride as the eluent.

Methods for converting iodo precursor 44 into the dyes of the invention are illustrated in Scheme (II):

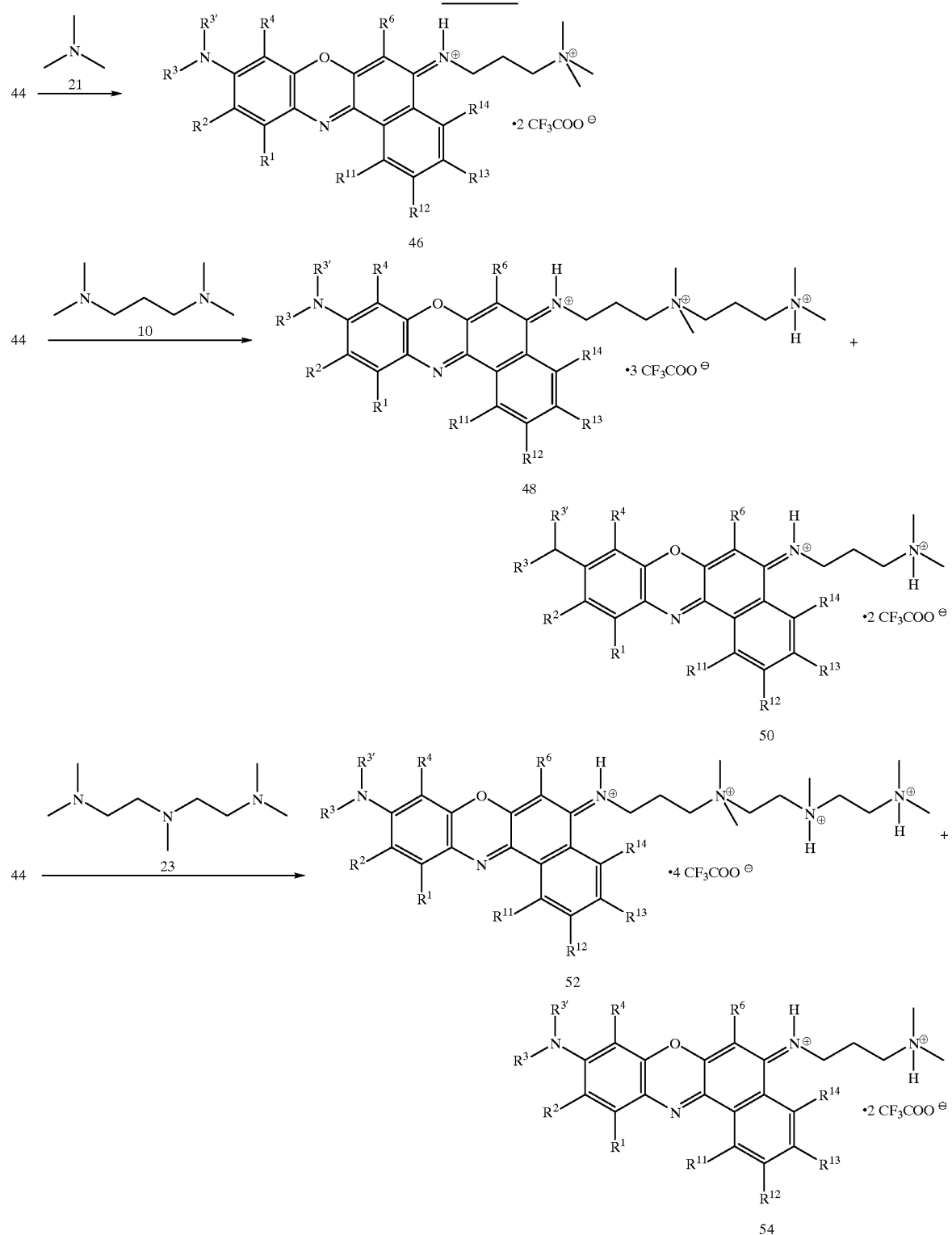

Referring to Scheme (II), the iodine atom of iodo precursor 44 is displaced with an aliphatic amine. The identity of the aliphatic amine depends upon the nature of the desired cation chain. For example, displacing the iodine atom with trimethylamine 21 yields dye 46 in which the terminal amino group of the cationic chain is a quaternary ammonium. Displacing the iodide atom with N,N,N',N'-tetramethyl-1,3-diaminopropane 10 yields a mixture of dyes 48 and 50 having a quaternary internal ammonium group and/or a tertiary terminal amino group. Displacing the iodide atom with N,N,N',N',N"-pentamethyldiethylenetriamine 23 yields a mixture of dyes 52 and 54 having two internal amino groups—one quaternary and one tertiary—and/or a tertiary terminal amino group. Conditions for carrying out the illustrated reactions and methods for isolating the dye products are provided in the Examples section.

Schemes (I) and (II) illustrate the synthesis of dyes having certain exemplary cationic chains. Those of skill in the art will recognize that dyes having other cationic chains can be readily obtained using the appropriate diiodoalkyl and aliphatic amine starting materials. For example, a variety of different iodo precursors having different numbers of methylene groups separating the C7 imminium nitrogen and iodine atoms can be obtained by reacting compound 42 with a diiodoalkylene having the structure I—$(CH_2)_n$—I, where n is the desired number of intervening methylene groups. The number of methylene groups separating the nitrogen atoms of the various internal amino groups from one another, as well as from the terminal amino group, can be adjusted in a similar fashion by choosing an appropriate aliphatic amine to displace the iodine atom of the iodo precursor. The saturation level of the cationic chain can likewise be adjusted by the appropriate choice of diiodoalkyl and aliphatic amine reactants.

Schemes (I) and (II) are particularly convenient for synthesizing the dyes of the invention because, with the exception of amino groups, the various R substituents do not require protection. Amino groups can be conveniently protected with Fmoc or other common base-labile amino protecting groups according to well-known methods (see, e.g., Greene & Wuts, 1991, Protective Groups in Organic Synthesis, John Wiley & Sons, New York, N.Y.).

Methods for synthesizing certain preferred compounds of the invention are provided in the Examples section.

5.5 Methods of Using the Compounds

The new [8,9]benzophenoxazine dyes of the invention can be used to label or stain nucleic acids for subsequent detection in a broad range of applications. For example, the dyes can be used to stain nucleic acids in solutions, in electrophoretic gels, in blotting applications, etc. In use, a dye of the invention is combined with a sample that contains a nucleic acid, incubated for a period of time sufficient to obtain a detectable fluorescent signal and observing the fluorescent signal.

The dye can be added directly to the sample, but is typically present as a component of an aqueous staining solution that is biologically compatible with the sample. The staining solution is made by dissolving the dye directly in an aqueous solvent such as water, a buffer solution (e.g., phosphate buffered saline; "PBS") or cell culture medium, a water-miscible organic solvent or a mixture comprising an aqueous solvent and a water-miscible organic solvent. Useful water-miscible organic solvents include, but are not limited to, dimethylsulfoxide (DMSO), dimethylformamide (DMF), N-methylpyrrolidone (NMP), lower alcohols (e.g., ethanol, propanol, isopropanol, etc.) and acetonitrile. As the dyes of the invention are water-soluble, the dye is usually first dissolved in an aqueous solution at a concentration of about 1,000 to 10,000 times greater than that desired for use in the staining solution and then diluted one or more times with an aqueous solvent, such as biological cell medium or PBS (pH 7.4) to yield a staining solution containing an effective amount of dye. An effective amount of dye is an amount sufficient to give a detectable fluorescent signal when in the presence of nucleic acids.

While not intending to be bound by any particular theory of operation, it is believed that the ability of the dyes of the invention to permeate cell membranes and/or bind nucleic acids is due, in part, to positive charges on the cationic chain. While the net charge of the cationic chain may be influenced/affected by a variety of factors, including, e.g., the pH of the staining solution, the use of a particular pH is not critical for success. The dyes of the invention are able to permeate cells and/or bind nucleic acids to produce detectable fluorescence signals over a broad range of pH values. Thus, nucleic acids may be stained with the dyes of the invention using pHs that are conventional for the particular application. Most nucleic acid staining assays may be performed at a pH in the range of pH 6 to pH 8–9. Thus, staining solutions for in vitro applications such as staining electrophoretic gels, will typically have a pH in this same range. Staining solutions for in vivo applications involving live-cell assays are preferably maintained at the same pH as that of the cell culture medium, typically around pH 7.4.

Typically, staining solutions for cellular samples have a dye concentration greater than about 0.1 nM and less than about 100 $\mu$M, more typically greater than about 1 nM. Preferably, the staining solution will contain about 1 nM to 20 nM dye. Staining solutions for electrophoretic gels typically have a dye concentration of greater than about 1 $\mu$M and less than about 10 $\mu$M, more typically about 4–5 $\mu$M. While the above-described staining solutions provide general guidelines, it is understood in the art that the specific dye concentration in a staining solution is determined by, among other things, the physical nature of the sample, the concentration of nucleic acids present and the nature of the analysis being preformed. The dye concentration necessary to perform a specific assay will therefore depend upon the assay, and is readily determinable by those having skill in the art.

The staining solution is combined with a sample that contains a nucleic acid. The nucleic acid in the sample may be either RNA or DNA, or a mixture thereof. Alternatively, the sample may contain analogs of RNA and/or DNA that have staining characteristics similar to those of RNA and/or DNA. When the nucleic acid is DNA (or a analog thereof), it may be present in any degree of strandedness, e.g., single-, double-, triple or quadruple-stranded. The nucleic acid may be either natural (i.e., biological in origin) or synthetic (i.e., prepared artificially), and may be present in the sample in its native state, such as in the form of an mRNA or a condensed chromosome, or in a non-native state, such as in the form of a denatured nucleic acid.

The nucleic acid can be virtually any length, from an oligonucleotide comprising as few as 10–40 nucleotides or base pairs, to a polynucleotide comprising in the range of hundreds to thousand of nucleotides or base pairs, to cDNAs, genes and even whole chromosomes. The nucleic acid may be homogeneously dispersed throughout the entire sample, for example dissolved in a nucleic acid solution, or may be present in only a part of the sample, for example sequestered in a electrophoretic gel band or in a cell or portion of a cell, and can therefore be used to distinguish between individual samples or to differentiate a portion or region within a single sample.

As a significant advantage of the [8,9]benzophenoxazine dyes of the invention is their permeability to cells, the nucleic acid may be enclosed in a biological structure, for example enclosed within a viral particle, an organelle or within a cell. Nucleic acids enclosed in biological structures can be obtained from a wide variety of environments, including, but not limited to, cultured cells, organisms or tissues, unfiltered or separated biological fluids (e.g., urine, cerebrospinal fluid, blood, lymph fluids, etc.), tissue homogenates, mucous, saliva, stool, physiological secretions, soil, water and air. The nucleic acid may be endogenous to the sample or it may be introduced as foreign material, such as by infection or transfection. Whole cells can be stained live or dead, and may be first fixed and treated according to routine histochemical or cytochemical procedures.

The sample may be combined with the staining solution via any means that facilitates contact between the dye and the nucleic acid. The contact can occur upon simple mixing, as in the case where the sample is a solution, or upon incubation of a structure containing the nucleic acid with the staining solution, as in the case of staining nucleic acids embedded in electrophoretic gels or other matrices. While the dyes of the invention have been shown to permeate cell membranes rapidly and completely upon addition of the staining solution to a cell sample, any other technique that is suitable for transporting the dye across a membrane, preferably with minimal disruption of the cell and/or membrane integrity, can also be used in conjunction with the dyes. Exemplary techniques involve the use of chemical agents (detergents, enzymes, adenosine triphosphate), receptor- or transport-proteins, pore-forming proteins, micro injection, electroporation, hypoosmotic shock, scrape loading, particle bombardment, etc.

The sample is incubated in the presence of the dye for a time period sufficient to produce a detectable fluorescence signal. While not intending to be bound by any theory of operation, since the dyes of the invention exhibit significant increases in quantum yield in the presence of nucleic acids, it is believed that the detectable fluorescence signal is caused upon formation of a nucleic acid-dye complex. Detectable fluorescence in a solution of nucleic acids is essentially instantaneous. Detectable fluorescence within cell membranes requires the dye to permeate into the cell. In general, visibly detectable fluorescence can be obtained in a wide variety of cells with embodiments of the invention within about 5 min. of combining the cells with a staining solution comprising about 1 nM to 10 nM dye.

Following staining, the staining solution may be removed and, depending upon the application, the nucleic acid rinsed prior to detection. For example, in electrophoretic applications, the stained gel can be rinsed (e.g., with water or buffer) prior to detection. However, owing to their large increase in quantum yield upon binding or complexing with nucleic acids, the unbound dye need not be removed prior to detection. This property of the dyes renders them invaluable for analyzing nucleic acids in live cells by static and/or flow cytometry, where the staining solution is not removed prior to detection. While permeation and fluorescence is rapid for most embodiments, it will be readily apparent to those of skill in the art that the time necessary for sufficient formation of a detectable fluorescence signal is dependent upon, among other factors, the physical and chemical nature of the individual sample and the sample medium.

The nearly universal membrane-permeability of the dyes of the invention and their rapid uptake kinetics enables the examination of nucleic acids in a wide variety of living samples. Virtually any cell type can be probed using the dyes of the invention, including prokaryotes such as bacteria and eukaryotes such as mammalian cells. In some cell lines, e.g., HCT-116, the dyes are particularly useful as they specifically stain the nucleus of these cells.

Like many nucleic acids stains, the [8,9] benzophenoxazine dyes of the invention exhibit enhanced fluorescence in the presence of nucleic acids. The spectral properties of the [8,9]benzophenoxazine dyes, including quantum yield in the absence of nucleic acids, are shown in Table 1. Typically the quantum yield increases significantly in the presence of nucleic acids. Compared with available red-emitting live-cell dyes, the dyes of the invention have improved quantum yields upon binding to nucleic acids.

Figure 2:
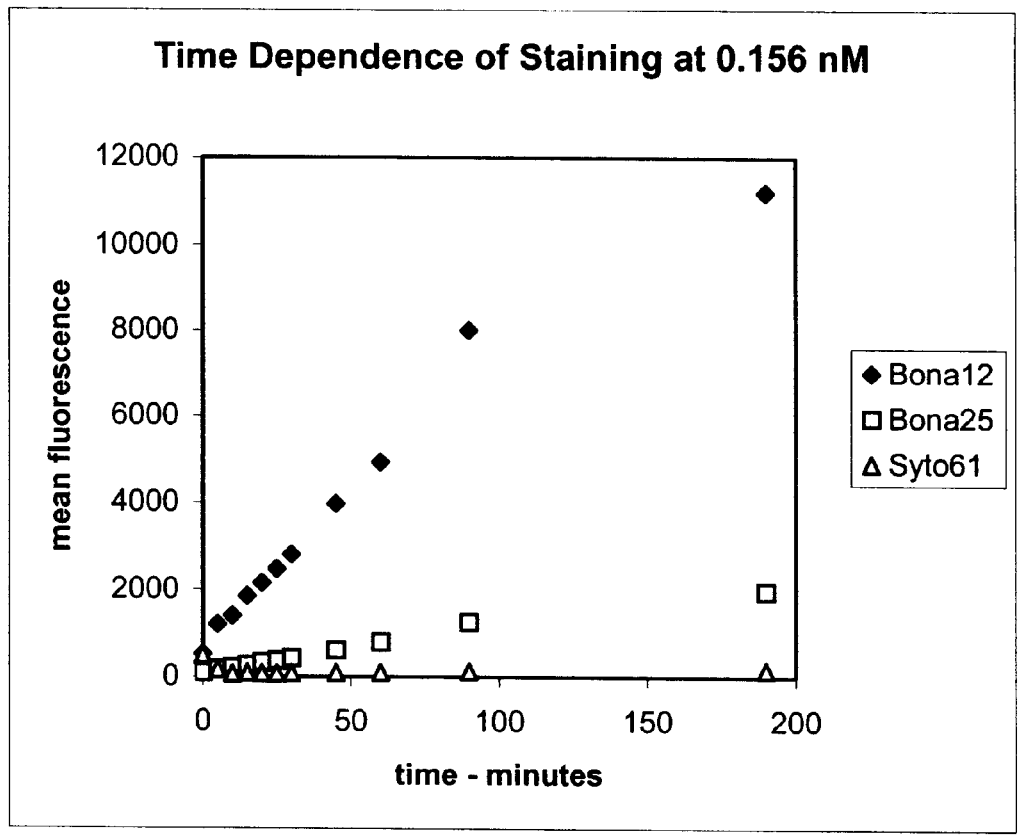
FIG. 2 is a graph illustrating the faster staining kinetics and brighter fluorescence signals achieved with dyes Bona 12 and Bona 25 as compared with commercially available SYTO 61® (Molecular Probes, Eugene, Oreg.) (all dyes at 0.156 nM).

Moreover, the dyes of the invention exhibit significantly faster permeation kinetics than currently available red-emitting live-cell stains, generally being taken up signficantly faster than SYTO 61® (Molecular Probes, Eugene, Oreg.). FIG. 2 shows that Bona 12 and Bona 25 dyes generate significant, detectable fluorescence in approximately 5 minutes, while SYTO 61 requires approximately 1 to 2 hours. These improvements in quantum yield and permeation kinetics translate directly into improved speed and sensitivity in nearly every area of nucleic acid detection.

While not every embodiment of the dyes of the invention will exhibit improvements in quantum yield and/or permeation kinetics relative to previously known nucleic acid stains, other attributes of the dyes of the invention represent significant improvements in other aspects of use, including the ability to selectivity tune their excitation and/or emissions bands to suit specific instruments, e.g., laser excitation frequencies, and/or their increased photostability. Quite significantly, all of the dyes of the invention excite and emit in the red region of the visible spectrum ($\geq 630$ nm) and are highly photostable. Dyes having 5 rings in the fused ring system emit at wavelengths higher than 700 nm. Currently, there are no commercially available, photostable live-cell nucleic acid stains whose emissions maxima are higher than 700 nm.

The nucleic acids are detected based upon the excitation and emissions spectral properties of the nucleic acid-dye complex. Generally, the stained sample is excited by a light source, such as a laser, capable of generating light at a wavelength at or near the excitation maximum of the nucleic acid-dye complex. The nucleobases of cellular nucleic acids and/or other cellular components such as proteins absorb ultraviolet light ($\lambda_{max}$=260–280 nm) with high molar absorptivities. Consequently, the visible red excitation profiles of the dyes of the invention provide a significant advantage, as most of these cellular components do not absorb (i.e., are transparent to) red light.

The fluorescence of the nucleic acid-dye complex is detected qualitatively or quantitatively by detecting the resultant light emission at a suitable wavelength. As the dyes of the invention fluoresce in the red region of the visible spectrum, the fluorescence signal is typically detected at wavelengths greater than about 650 nm. Dyes having higher emissions maxima can be detected at even higher wavelengths. The emission may detected by means that include, by way of example and not limitation, visible inspection, photographic film, fluorimeters, quantum counters, plate readers, epifluorescence microscopes and static and flow cytometers. The emitted light can be detected directly, or it may first be amplified, such as by first allowing it to pass through a photo multiplier. For quantitative detection. the emitted photons can be counted with photon counter.

The sensitivity, permeability, photostability and excitation and emission properties of the dyes of the invention provide universal utility in all assays involving staining of nucleic acids, as well as substantial improvements over currently available live-cell and other nucleic acid stains. The ability to rapidly detect and/or quantify nucleic acids in any solution, on any substrate, and/or from any sample, and in particular from live-cell samples using red lasers, offers unparalleled opportunities in fields that utilize fluorescent staining of nucleic acids.

6. EXAMPLES

The invention having been described, the following Examples are offered by way of illustration, and not limitation.

6.1 Compound Syntheses
6.1.1 Synthesis of Bona 11 and Bona 12

[8,9]Benzophenoxazine dyes Bona 11 and Bona 12 were synthesized as illustrated in Scheme (III), below:

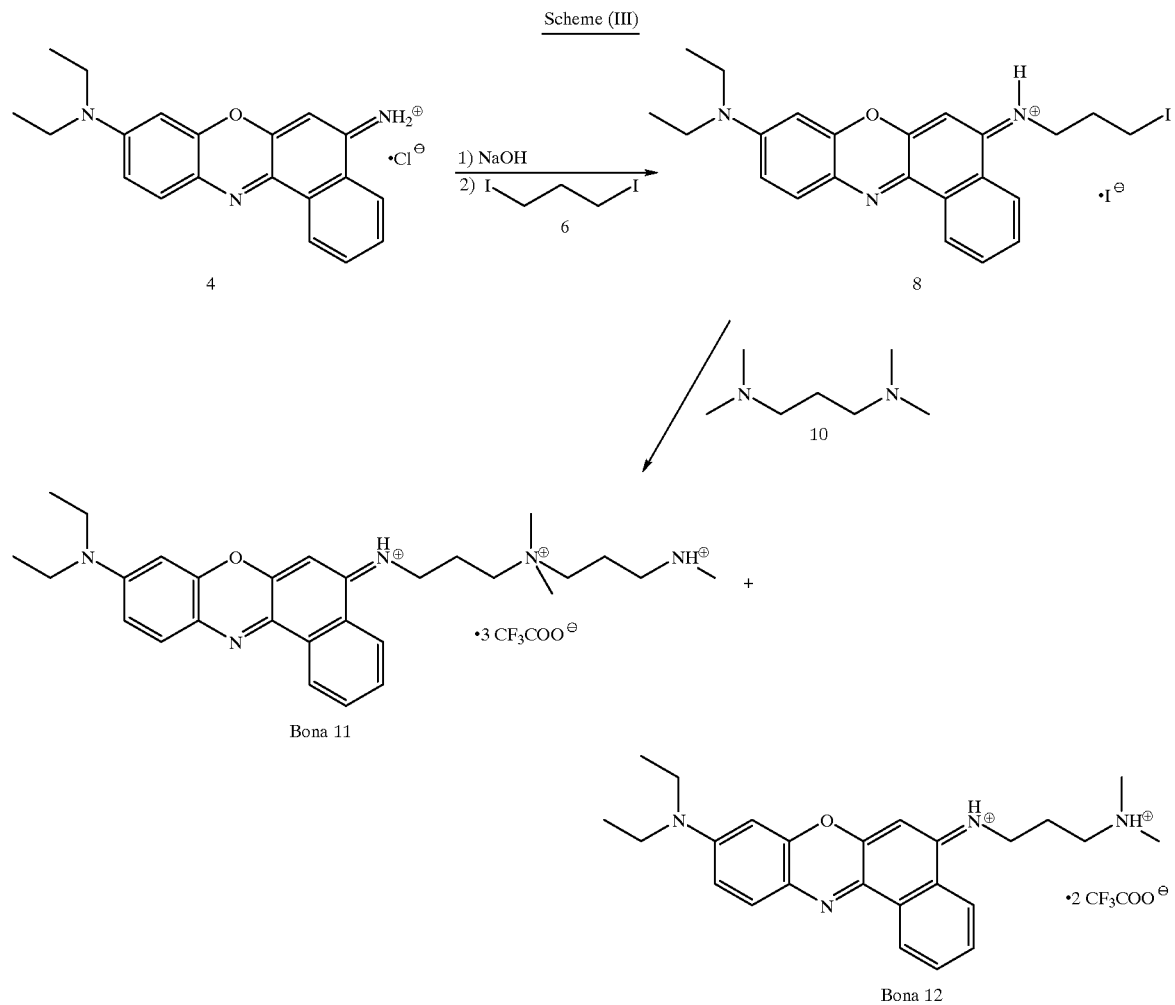

Scheme (III)

Referring to Scheme (III), 1.18 g of Nile Blue Chloride (4, Aldrich) was suspended in 100 ml of water at 60° C. for 30 min. 100 ml of 0.5 M aqueous NaOH was added. The basic Nile Blue was extracted with methylene chloride (3 times, 100 ml each time) and the combined extracts dried with brine followed by anhydrous $Na_2SO_4$. Following removal of the solvent removed by evaporation, the residual (basic Nile Blue) was dried overnight under vacuum.

In a 50-ml round-bottomed flask, 64 mg of the basic Nile blue (0.2 mmol) was dissolved in 5 ml of anhydrous toluene. 230 ml of diiodopropane (6; 2 mmol; Aldrich) was added. The mixture was refluxed under argon for 16 hr. 88.1 mg of Compd. 8 was obtained (yield 72%) by flash silica gel column chromatography using 5% (v/v) methanol in methylene chloride as the eluent. Compd 8 MS (M+H): calculated: 486.1; found: 486.3.

In a 50-ml round-bottomed flask, 10 mg of Compd. 8 (16 mmol) was dissolved in 10 ml of anhydrous ethanol, 17.2 ml of N,N,N',N'-tetramethyl-1,3-diaminopropane (10; 103 mmol, Aldrich) was added and the mixture was refluxed under argon for 6 hr, yielding a mixture of Bona 11 and Bona 12. The two dyes were isolated via reverse-phase HPLC using a linear gradient (0%–70% over 30 min.) of Buffer B (0.085% TFA in acetonitrile) in Buffer A (0.1% TFA in water) as the eluent. In this gradient, dye Bona 11 eluted at 14.8 min.; dye Bona 12 eluted at 16.1 min.

Bona 11 MS (M+H): calculated: 488.3; found: 488.0. MS-MS Fragmentation: 403.2, 358.2, 349.8. 330.0, 303.2, 286.0, 259.2, 86.0, 58.0.

Bona 12 MS (M+H): calculated: 403.2; found: 403.0. MS-MS Fragmentation: 403.2, 358.2. 330.0, 303.2, 286.2, 259.2, 86.0, 58.0.

6.1.2 Synthesis of Dye Bona 2

[8,9]Benzophenoxazine dye Bona 2 was synthesized as illustrated in Scheme (IV), below:

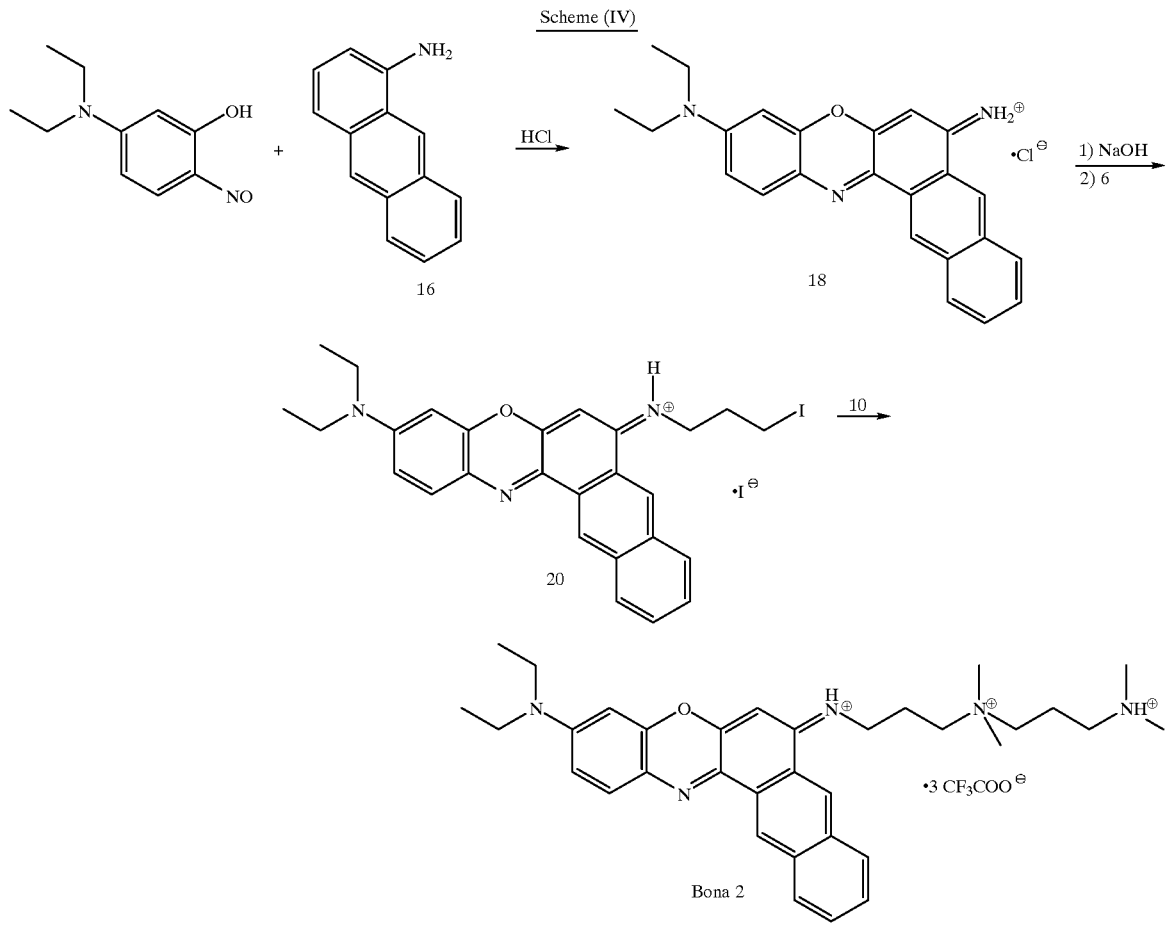

Scheme (IV)

Referring to Scheme (IV), in a 250-ml round-bottomed flask, 1.16 g of 2-nitroso-5-diethylaminophenol hydrochloride (14; 5 mmol; TCI America) and 0.97 g of 1-aminoanthracene (16; 4.5 mmol; ~90%, purity; Aldrich) were dissolved in 100 ml of ethanol with 3 ml of concentrated HCl (37%) and the mixture refluxed for 2 hours. 1.62 g of Compd. 18 (Yield 89%). was obtained via flash silica gel column chromatography using methanol/methylene chloride as the eluent.

Compd. 18 MS (M+H): calculated: 368.2; found: 368.2.
$^1$H-NMR of Compd. 18 (in DMSO-d6; ppm): 1.12 (triplet, 6H), 3.40 (multiplet, 4H), 6.42 (duplet, 2H), 6.58 (d, 1H), 7.40(d, 1H), 7.60 (m, 2H), 8.15 (m, 2H), 8.9 (d, 2H) and 10.10 (broad singlet, 1H).

101 mg of Compd. 18 (0.25 mmol) was dissolved in 10 ml of methanol, 90 ml of methylene chloride was added and the solution was washed with 50 ml of 1M NaOH (twice) followed by 50 ml of brine (once) in a separatory funnel. The organic layer was dried with anhydrous Na$_2$SO$_4$. After the solvent was evaporated, the residue was dried with an oil pump for 6 hours. The dried residue was then dissolved in 20 ml of toluene, 345 mL of 1,3-diiodopropane (6, 3 mmol) was added and the mixture was refluxed under argon for 16 hours. 95 mg of Compd. 20 (Yield 57%) was obtained via flash silica gel column chromatography using 5% (v/v) methanol in methylene chloride as the eluent.

Cmpd. 20 MS (M+H): calculated: 536.1; found: 536.3.
$^1$H-NMR of Compd. 20 (in DMSO-d6; ppm): 1.19 (t, 6H), 3.19 (m, 2H), 3.45 (m, 2H), 3.56 (quadruplet, 4H), 3.78 (m, 2H), 6.742 (s, 1H), 6.930 (s, 1H), 7.105 (m, 1H), 7.74 (m, 3H), 8.10 (d, 1H), 8.26 (d, 1H), 9.065 (s, 1H), 9.219 (s, 1H) and 10.353 (broad singlet, 1H).

In a 25-ml round-bottomed flask, 27 mg of Compd. 20 (0.041 mmol) was dissolved in 5 ml anhydrous ethanol, 34 ml of N,N,N',N'-tetramethyl-1,3-diaminopropane (10; 0.204 mmol; Aldrich) was added and the mixture was refluxed under argon for 4 hours. After the ethanol was evaporated, the residue was dissolved in 15 ml H$_2$O with 0.5 ml trifluoroacetic acid (TFA) and washed 5 times with ethyl acetate (50 ml each time) to remove the starting materials. The aqueous solution was then concentrated and run through a gel-filtration column (Sephadex G-10). 5% Aqueous acetic acid solution was applied as the eluent. After the solvents were evaporated, 9.1 mg of pure Bona 2 was obtained (yield 31%). Bona 2 MS (M+H): calculated: 538.3; found: 538.0. MS-MS Fragmentation: 538.2, 408.2, 380.2, 336.0, 86.01, 58.0.

6.1.3 Synthesis of Dyes Bona 22, Bona 24 and Bona 25

[8,9]Benzophenoxazine dyes Bona 22, Bona 24 and Bona 25 were synthesized as illustrated in Scheme (V), below:

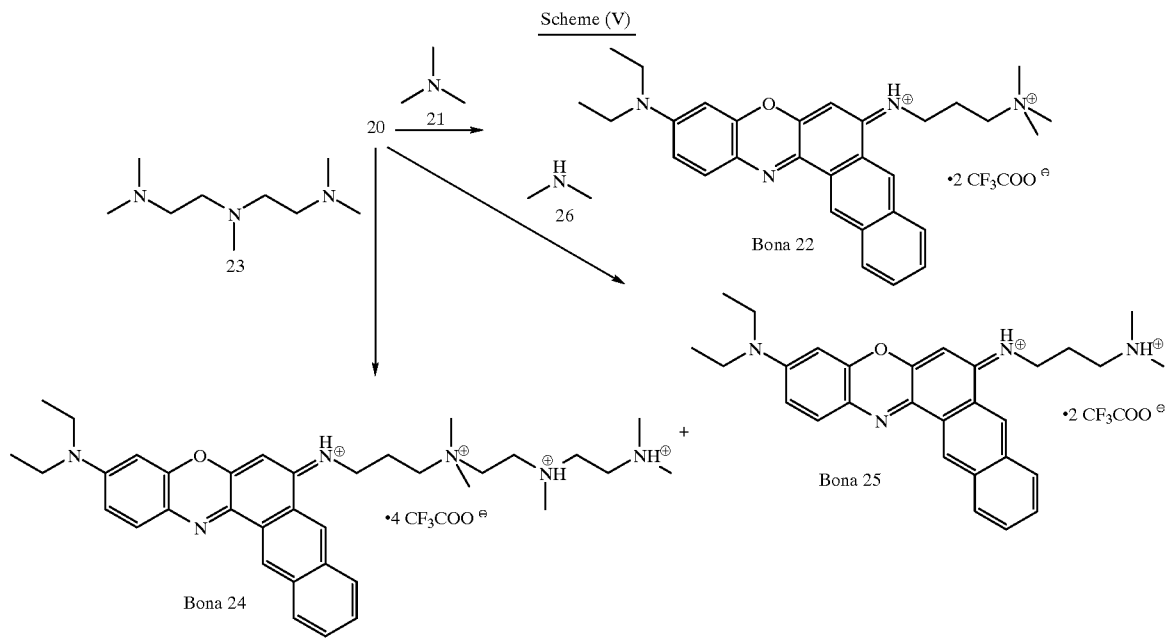

Scheme (V)

Bona 22

In a 25-ml round-bottomed flask, 3.0 mg of Compd. 20 (4.5 mmol; prepared as described in Section 6.1.2, supra) was dissolved in 2 ml anhydrous ethanol, 2.86 ml of trimethylamine (21; 45.2 mmol; Aldrich,) was added and the mixture was refluxed under argon for 4 hours. After the ethanol was evaporated, the residual was dissolved in 0.1% aqueous TFA, and purified by HPLC as described in Section 6.1.1, supra. 1.9 mg of pure Bona 22 was obtained (Yield 61%; retention time 17.0 min). Bona 22 MS (M+H): calculated: 467.3; found: 467.1. MS-MS Fragmentation: 467.4, 408.2, 380.0, 336.2.

Bona 24 and Bona 25

In a 25-ml round-bottomed flask, 1.5 mg of Compd. 20 (2.3 mmol; prepared as described in Section 6.1.2, supra) was dissolved in 3 ml of anhydrous ethanol, 20.8 ml of N,N,N',N',N"-pentamethyldiethylenetriamine (23; 0.1 mmol; Aldrich) was added and the mixture was refluxed under argon for 8 hours, yielding a mixture of dyes Bona 24 and Bona 25, which were purified by HPLC as described in Section 6.1.1, supra. Dye Bona 24 eluted at 17.8 min.; dye Bona 25 eluted at 19.2 min. The formation of dye Bona 25 was probably due to the fragmentation of Compd. 24 during the reflux conditions.

Bona 24 MS (M+H): calculated: 581.4; found: 581.3. MS (M/2+H): calculated: 291.1; found: 291.3. MS-MS Fragmentation: 581.2, 408.2, 129.2, 72.0.

Bona 25 MS (M+H): calculated: 453.3; found: 453.0. MS (M/2+H): calculated: 227.2; found: 227.3. MS-MS Fragmentation: 453.6, 408.2, 380.2, 363.8, 353.0, 336.4, 335.8, 309.4, 86.2, 72.2, 58.4.

Referring to Scheme (V), in an alternative method, dye Bona 25 was obtained as follows: in a 10 ml round-bottomed flask, 1 mg of Compd. 20 (1.5 mmol) was dissolved in 3 ml of 2 M dimethylamine in methanol (26; 6 mmol; Aldrich). The solution was refluxed under argon for 2 hours and pure Bona 25 was obtained by HPLC as described above.

6.1.4 Synthesis of Dyes Bona 27 and 28

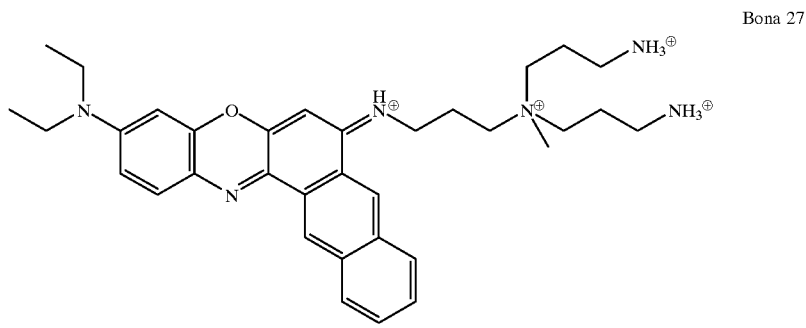

Bona 28

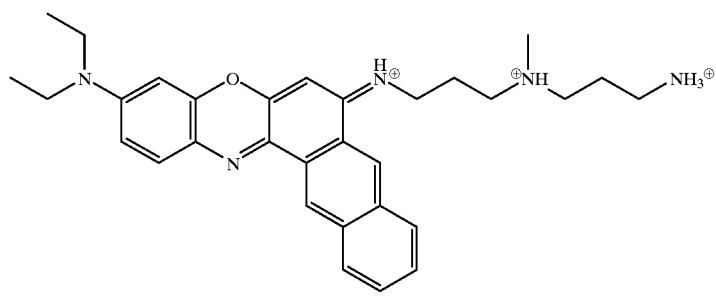

[8,9]Benzophenoxazine dyes Bona 27 and 28 (illustrated above), which have a primary terminal amino group, were synthesized from Compound 20 as illustrated in Scheme (V) using 3,3'-diamino-N-methyldipropylamine ($CH_3N(CH_2CH_2CH_2NH_2)_2$; Aldrich) as the alkyl amine. Briefly, in a 25-ml round-bottomed flask, 1.5 mg of Compd. 20 (2.3 mmol; prepared as described in Section 6.1.2, supra) was dissolved in 3 ml of anhydrous ethanol, 16.1 ml of 3,3'-diamino-N-methyldipropylamine (0.1 mmol) was added and the mixture was refluxed under argon for 8 hours, yielding a mixture of dyes Bona 27 and Bona 28. Pure Bona 27 and Bona 28 were obtained by HPLC as described in Section 6.1.1, supra. Dye Bona 27 eluted at 17.0 min.; dye Bona 28 eluted at 18.1 min.

Bona 27 MS (M+H): calculated: 553.4; found: 553.6. MS (M/2+H): calculated: 277.2; found: 277.5.

Bona 28 MS (M+H): calculated: 496.3; found: 496.5. MS (M/2+H): calculated: 248.7; found: 248.8.

6.2 Spectral Properties of the Dyes of the Invention

The absorbance (excitation) maxima ($\lambda_{abs, max}$), molar extinction coefficients ($\epsilon$), emission maxima ($\lambda_{em, max}$) and quantum yields (Q) of certain exemplary dyes of the invention in Tris buffer (pH 7.4) and/or methanol are provided in TABLE 1, below:

TABLE 1

Spectral Properties of Exemplary Dyes of the Invention

| Dye | Solvent | $\lambda_{abs, max}$(nm) | $\epsilon(M^{-1}cm^{-1})$ | $\lambda_{em, max}$(nm) | Q |
|---|---|---|---|---|---|
| Bona 11 | Methanol | 639 | 64,000 | 666 | 0.021 |
|  | Tris Buffer | 648 639 | 54,000 51,000 | 682 | 0.0077 |
| Bona 12 | Methanol | 637 |  | 665 | 0.028 |
|  | Tris Buffer | 648 |  | 678 | 0.0072 |
| Bona 2 | Methanol | 656 |  | 698 | 0.0093 |
|  | Tris Buffer | 655 |  | 693 | 0.0070 |
| Bona 22 | Methanol | 656 |  | 695 | 0.013 |
|  | Tris Buffer | 655 |  | 711 | 0.0067 |
| Bona 24 | Methanol | 656 |  | 697 | 0.016 |
|  | Tris Buffer | 655 |  | 711 | 0.0058 |
| Bona 25 | Methanol | 656 | 58,000 | 694 | 0.033 |
|  | Tris Buffer | 654 629 | 54,000 63,000 | 709 | 0.0075 |
| Bona 27 | Methanol | 660 582 |  | 699 | 0.013 |
|  | Tris Buffer |  |  |  |  |
| Bona 28 | Methanol | 655 |  | 694 | 0.026 |
|  | Tris | 655 |  | 709 | 0.0049 |

TABLE 1-continued

Spectral Properties of Exemplary Dyes of the Invention

| Dye | Solvent | $\lambda_{abs, max}$(nm) | $\epsilon(M^{-1}cm^{-1})$ | $\lambda_{em, max}$(nm) | Q |
|---|---|---|---|---|---|
|  | Buffer | 630 |  |  |  |

6.3 The Dyes of the Invention Diffuse Across Cell Membranes

This example demonstrates the ability of the dyes of the invention to passively permeate through, or diffuse across, membranes of live cells.

6.3.1. Experimental Protocol

HCT-116 colorectal cells were plated at a density of approx. 10,000 cells/well in a 96-well microtiter plate (Costar 3603) in a volume of 200 µl medium (RPMI 1640 medium with 10% fetal bovine serum). Penicillin/streptomycin were added to inhibit bacterial infections in the cell culture. After the cells had attached to the plate matrix (overnight incubation), the cells were stained with 50 µl staining solution (1–10 nM dye in either medium, PBS or a calcium buffer containing 12.5 mM $CaCl_2$, 140 mM NaCl and 10 mM Hepes, pH 7.4). Images of the cells were collected immediately after staining on an FMAT 8100 HTS Instrument (PE Biosystems, Foster City, Calif.).

6.3.2 Results

The results of the membrane permeability experiment are provided in TABLE 2

TABLE 2

Permeability Characteristics of Dyes of the Invention

| Emission Wavelength (nm) | Dye | Permeability |
|---|---|---|
| 650–680 | Bona 11 | Excellent |
| 650–680 | Bona 12 | Excellent |
| 680–730 | Bona 2 | No |
| 680–730 | Bona 22 | Good |
| 680–730 | Bona 24 | Excellent |
| 680–730 | Bona 25 | Excellent |
| 680–730 | Bona 27 | No |
| 680–730 | Bona 28 | No |

As indicated in TABLE 2, dyes Bona 11, Bona 12, Bona 24 and Bona 25 exhibited excellent membrane permeability. Dye Bona 22 exhibited good membrane permeability. Dyes Bona 2, Bona 27 and Bona 28 were impermeable to cell membranes.

Similar experiments performed with UC11 (astrocytoma), COS (monkey kidney), CHO (Chinese hamster ovary) and HUVEC (human umbilical vein endothelial) cell provided similar results.

6.4 The Dyes of the Invention Stain Nucleic Acids in Whole Cells

HCT-116 cells were stained as previously described in Section 6.3.1, supra, with dyes Bona 12 (20 nM), Bona 24 (20 nM), Bona 25 (20 nM) and commercially available SYTO 61® (4 nM; Molecular Probes, Eugene, Oreg.). As a control, cells were also stained with 0.57 µg/µl antibody HLA-A,B,C (Pharmingen) that had been labeled with the cyanine dye Cy5 (Cy5-NHS ester; Amersham).

The results of the live-cell staining experiment are provided in FIGS. 1A–D. FIG. 1A shows cells stained with the labeled antibody, which binds to membrane receptors, and therefore illuminates the entire cell. In FIG. 1A, the whole cells are clearly visible. In comparison, in FIGS. 1B, C and D, which show cells stained with Bona 12, Bona 24 and Bona 25, respectively, the area stained is much smaller and more localized, indicating that the dyes are penetrating the nuclear membranes and staining the nuclei of the cells. In cells stained with SYTO 61® (FIG. 1E), a larger area of the cells is visible, much like cells stained with labeled antibody. Thus, this experiment demonstrates that the dyes of the invention are brighter and more specific for nucleic acids than commercially available red-emitting dye SYTO 61®.

6.5 The Dyes of the Invention Are Brighter and Have Superior Staining Kinetics Than Available Red-emitting Live-cell Nucleic Acid Stains HCT-116 cells were stained as described in Section 6.3.1, supra, with 0.156 nM dyes Bona 12, Bona 25 and SYTO 61® and the mean fluorescence recorded as a function of time. A graph of the time-dependent fluorescence is provided in FIG. 2. At almost every time point, the dyes of the invention produced a brighter signal than SYTO 61®, indicating that the dyes of the invention permeate cell membranes faster than SYTO 61®. Quite significantly, at 200 min., the fluorescence signal from Bona 12 is more than four orders of magnitude greater than that of SYTO 61®; the signal from Bona 25 is more than three orders of magnitude greater.

The faster permeation kinetics and brighter signals are also observed at higher dye concentrations. In a similar experiment using 40 nM dyes (results not shown), it took only 5 minutes to label to a detectable level HCT-116 cells with Bona 25, as compared with 1 to 2 hrs for SYTO 61®.

It is evident from the various experiments described above that the new [8,9]benzophenoxazinc dyes of the invention provide a new and important class of fluorescent live-cell nucleic acid stains. The new dyes provide for significantly faster kinetics and brighter fluorescence than commercially-available SYTO 61®, allowing for the rapid detection of DNA in live-cell assays using less dye. The dyes also provide significant advantages due to their red excitation and emissions spectral properties. Excitation in the visible red region of the spectrum is advantageous because it minimizes autofluorescence from chromophores commonly found in cells (e.g., flavins, porphyrins, etc.), the Raman scattering of water and the fluorescence contributed by assay equipment, such as plastics. Thus, many compounds and/or substances that autofluoresce in the green are transparent in the red, thereby reducing background signals and also minimizing the possibility of compounds in the cells quenching the assay. Emission in the visible red region of the spectrum is advantageous because it permits the use of lower-cost detection equipment. Thus, the new dyes of the invention provide significant advantages in both in vitro and in vivo nucleic acid staining applications.

All publications, patents and patent applications mentioned in this specification are herein incorporated by reference to the same extent as if each individual publication, patent or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A benzophenoxazine compound according to structural formula (I):

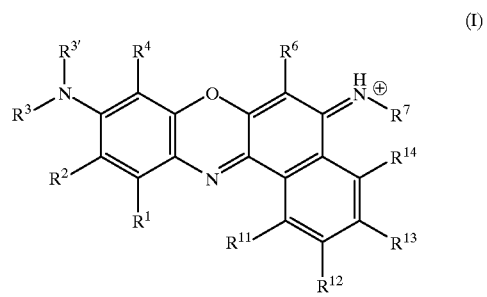

alone or in combination with a counter ion thereof, wherein:

$R^1$, when taken alone, is selected from the group consisting of hydrogen, halogen, $(C_1–C_6)$ alkyl, —OR', —SR', —NR'R', —CN, —NO$_2$ and —C(O)R', or when taken together with $R^2$ is $(C_5–C_{14})$ aryleno or $(C_5–C_{14})$ aryleno substituted with one or more of the same or different W groups;

$R^2$, when taken alone, is selected from the group consisting of hydrogen, $(C_1–C_6)$ alkyl, —OR', —SR', —NR'R', —CN, —NO$_2$ and —C(O)R', or when taken together with $R^1$ is $(C_5–C_{14})$ aryleno or $(C_5–C_{14})$ aryleno substituted with one or more of the same or different W groups;

$R^3$, when taken alone, is selected from the group consisting of hydrogen, $(C_1–C_6)$ alkyl and $(C_5–C_{14})$ aryl, or when taken together with $R^{3'}$ is $(C_2–C_8)$ alkyldiyl or $(C_2–C_6)$ alkyleno;

$R^{3'}$, when taken alone, is selected from the group consisting of hydrogen, $(C_1–C_6)$ alkyl and $(C_5–C_{14})$ aryl or when taken together with $R^3$ is $(C_2–C_8)$ alkyldiyl or $(C_2–C_6)$ alkyleno;

$R^4$ is selected from the group consisting of hydrogen, $(C_1–C_6)$ alkyl, —OR', —SR', —NR'R', —CN, —NO$_2$ and —C(O)R';

$R^6$ is selected from the group consisting of hydrogen, $(C_1–C_6)$ alkyl, —OR', —SR', —NR'R', —CN, —NO$_2$ and —C(O)R';

$R^7$ is an aliphatic cationic chain comprising a total of about 4 to 20 non-hydrogen atoms and from 1 to 4 heteroatomic groups which are positively charred at a pH in the range of about pH 6 to pH 9;

$R^{11}$, when taken alone, is selected from the group consisting of hydrogen, $(C_1–C_6)$ alkyl, —OR', —SR', —NR'R', —CN, —NO$_2$ and —C(O)R', or when taken together with $R^{12}$ is $(C_5–C_{14})$ aryleno or $(C_5–C_{14})$ aryleno substituted with one or more of the same or different W groups;

$R^{12}$, when taken alone, is selected from the group consisting of hydrogen, $(C_1–C_6)$ alkyl, —OR', —SR', —NR'R', —CN, —NO$_2$ and —C(O)R', or when taken together with $R^{11}$ or $R^{13}$ is $(C_5–C_{14})$ aryleno or $(C_5–C_{14})$ aryleno substituted with one or more of the same or different W groups;

R$^{13}$, when taken alone, is selected from the group consisting of hydrogen, (C$_1$–C$_6$) alkyl, —OR', —SR', —NR'R', —CN, —NO$_2$ and —C(O)R', or when taken together with R$^{12}$ or R$^{14}$ is (C$_5$–C$_{14}$) aryleno or (C$_5$–C$_{14}$) aryleno substituted with one or more of the same or different W groups;

R$^{14}$, when taken alone, is selected from the group consisting of hydrogen, (C$_1$–C$_6$) alkyl, —OR', —SR', —NR'R', —CN, —NO$_2$ and —C(O)R', or when taken together with R$^{13}$ is (C$_5$–C$_{14}$) aryleno or (C$_5$–C$_{14}$) aryleno substituted with one or more of the same or different W groups;

each W is independently selected from the group consisting of (C$_1$–C$_6$) alkyl, —OR', —SR', —NR'R', —CN, —NO$_2$ and —C(O)R'; and each R' is independently hydrogen or (C$_1$–C$_6$) alkyl.

2. The benzophenoxazine compound of claim 1 which is membrane permeable.

3. The benzophenoxazine compound of claim 1 in which R$^1$, R$^2$, R$^4$ and R$^6$ are each hydrogen.

4. The benzophenoxazine compound of claim 1 in which R$^3$ and R$^{3'}$ are each independently (C$_1$–C$_3$) alkanyl.

5. The benzophenoxazine compound of claim 1 in which R$^{11}$, R$^{12}$, R$^{13}$ and R$^{14}$ are each hydrogen.

6. The benzophenoxazine compound of claim 1 in which R$^{11}$ is taken together with R$^{12}$ and is benzo.

7. The benzophenoxazine compound of claim 1 in which R$^{12}$ is taken together with R$^{13}$ and is benzo.

8. The benzophenoxazine compound of claim 1 in which R$^{13}$ is taken together with R$^{14}$ and is benzo.

9. The benzophenoxazine compound of claim 1 in which R$^7$ is selected from the group consisting of —(CH$_2$)$_n$—NRRR, —(CH$_2$)$_n$—NRR—(CH$_2$)$_n$—NRRR and —(CH$_2$)$_n$—NRR—(CH$_2$)$_n$—NRR—(CH$_2$)$_n$—NRRR, where each n is independently an integer from 2 to 3 and each R is independently selected from the group consisting of hydrogen and (C$_1$–C$_3$) alkanyl.

10. The benzophenoxazine compound of claim 1 which is a compound according to structural formula (II):

(II)

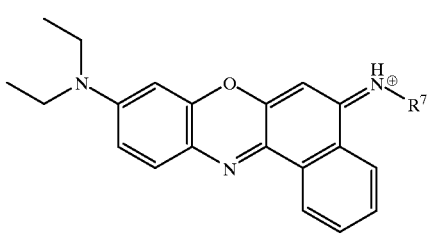

alone or in combination with a counter ion thereof, wherein R$^7$ is as defined in claim 1.

11. The benzophenoxazine compound of claim 10 which is membrane permeable.

12. The benzophenoxazine compound of claim 10 in which R$^7$ is selected from the group consisting of —(CH$_2$)$_n$—NRRR, —(CH$_2$)$_n$—NRR—(CH$_2$)$_n$—NRRR and —(CH$_2$)$_n$—NRR—(CH$_2$)$_n$—NRR—(CH$_2$)$_n$—NRRR, where each n is independently an integer from 2 to 3 and each R is independently selected from the group consisting of hydrogen and (C$_1$–C$_3$) alkanyl.

13. The benzophenoxazine compound of claim 10 which has the structural formula:

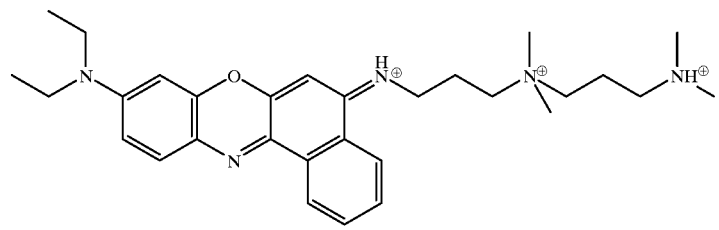

alone or in combination with a counter ion thereof.

14. The benzophenoxazine compound of claim 10 which has the structural formula:

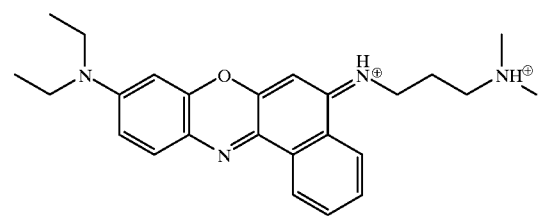

alone or in combination with a counter ion thereof.

15. The benzophenoxazine compound of claim 2 which is a compound according to structural formula (III):

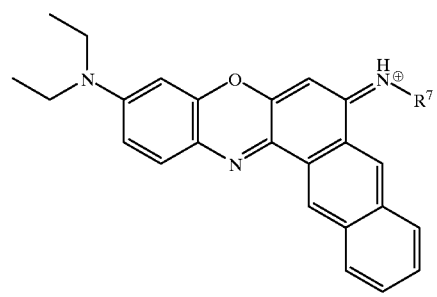

alone or in combination with a counter ion thereof, wherein R$^7$ is as defined in claim 1.

16. The benzophenoxazine compound of claim 15 which is membrane permeable.

17. The benzophenoxazine compound of claim 15 in which R$^7$ is selected from the group consisting of —(CH$_2$)

$_n$—NRRR, —(CH$_2$)$_n$—NRR—(CH$_2$)$_n$—NRRR and —(CH$_2$)$_n$—NRR—(CH$_2$)$_n$—NRR—(CH$_2$)$_n$—NRRR, where each n is independently an integer from 2 to 3 and each R is independently selected from the group consisting of hydrogen and (C$_1$–C$_3$) alkanyl.

18. The benzophenoxazine compound of claim 15 which has the structural formula:

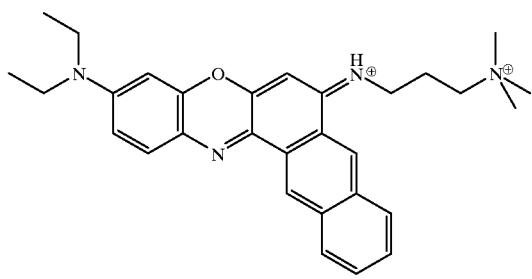

alone or in combination with a counter ion thereof.

19. The nucleic acid-staining dye of claim 15 which has the structural formula:

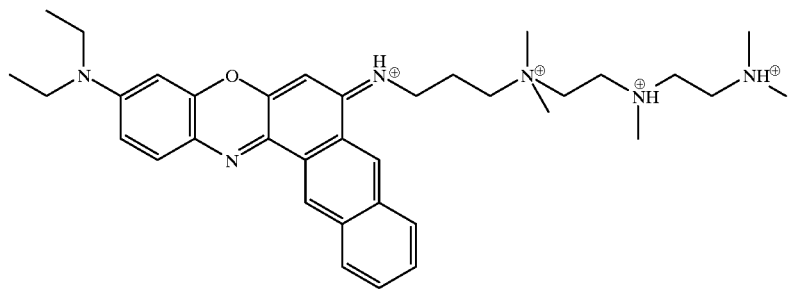

alone or in combination with a counter ion thereof.

20. The benzophenoxazine compound of claim 15 which has the structural formula:

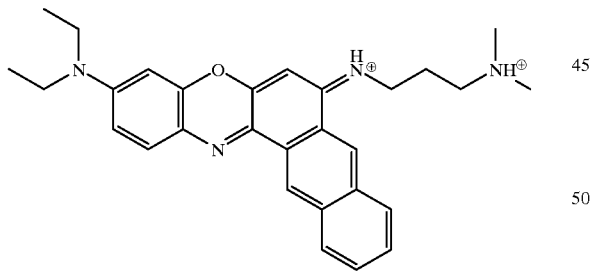

alone or in combination with a counter ion thereof.

21. A method of staining a nucleic acid, comprising the step of contacting the nucleic acid with a benzophenoxazine compound according to claim 1.

22. The method of claim 21 in which the nucleic acid is at least partially double-stranded.

23. The method of claim 21 in which the nucleic acid is a DNA.

24. The method of claim 21 in which the nucleic acid is an RNA.

25. The method of claim 21 in which the nucleic acid is enclosed within a biological structure.

26. The method of claim 25 in which the biological structure is a cell membrane.

27. The method of claim 21 in which the nucleic acid is embedded within a matrix.

28. The method of claim 21 in which the matrix is an electrophoretic gel.

29. A method of staining a nucleic acid in a biological sample comprising contacting the biological sample with a benzophenoxazine compound according to claim 1.

30. The method of claim 29 in which the biological sample comprises a whole cell and the nucleic acid-staining dye is membrane permeable.

31. The method of claim 20 in which the cell is a mammalian cell.

32. The method of claim 29 in which the nucleic acid is a DNA.

33. The method of claim 20 in which the cell is a eukaryotic cell.

34. The benzophenoxazine compound of claim 1 in which R$^1$ is taken together with R$^2$ and is benzo, (1,2)naphthaleno or (2,3)naphthaleno.

* * * * *

UNITED STATES PATENT AND TRADEMARK OFFICE
CERTIFICATE OF CORRECTION

PATENT NO.    : 6,140,500  
DATED         : October 31, 2000  
INVENTOR(S)   : Yan et al.

Page 1 of 1

It is certified that error appears in the above-identified patent and that said Letters Patent is hereby corrected as shown below:

<u>Title page,</u>
Item [75] Inventors: "Sheri Miragila" should read -- Sheri Miraglia --.

<u>Column 32,</u>
Line 47, "The benzophenoxazine compound of claim 2" should read -- The benzophenoxazine compound of claim 1 --.

<u>Column 34,</u>
Lines 11 and 15, "The method of claim 20" should read -- The method of claim 30 --.

Signed and Sealed this

Nineteenth Day of February, 2002

Attest:

Attesting Officer

JAMES E. ROGAN  
*Director of the United States Patent and Trademark Office*